(12) United States Patent
Kumar

(10) Patent No.: US 8,986,732 B2
(45) Date of Patent: *Mar. 24, 2015

(54) BIPHASIC LIPID-VESICLE COMPOSITIONS AND METHODS FOR TREATING CERVICAL DYSPLASIA BY INTRAVAGINAL DELIVERY

(71) Applicant: Helix BioPharma Corporation, Aurora (CA)

(72) Inventor: Praveen Kumar, Kitchener (CA)

(73) Assignee: Helix BioPharma Corporation, Aurora (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/965,122

(22) Filed: Aug. 12, 2013

(65) Prior Publication Data

US 2015/0044274 A1 Feb. 12, 2015

(51) Int. Cl.
*A61K 9/127* (2006.01)
*A61K 38/21* (2006.01)

(52) U.S. Cl.
CPC ............... *A61K 9/127* (2013.01); *A61K 38/212* (2013.01)
USPC ......................................... 424/450; 424/85.7

(58) Field of Classification Search
None
See application file for complete search history.

(56) References Cited

U.S. PATENT DOCUMENTS

| | | | |
|---|---|---|---|
| 5,358,708 A | 10/1994 | Patel | |
| 5,576,017 A * | 11/1996 | Kim .............................. | 424/450 |
| 6,071,534 A | 6/2000 | Kim et al. | |
| 6,264,990 B1 | 7/2001 | Knepp et al. | |
| 6,656,499 B1 | 12/2003 | Foldvari et al. | |
| 7,629,384 B2 | 12/2009 | Fossel | |
| 2005/0037048 A1 | 2/2005 | Song | |
| 2009/0285880 A1 | 11/2009 | Hellerbrand et al. | |
| 2010/0086573 A1 | 4/2010 | Anderson | |
| 2010/0196453 A1* | 8/2010 | Foldvari et al. ............... | 424/450 |
| 2013/0216610 A1 | 8/2013 | Foldvari et al. | |
| 2013/0224283 A1 | 8/2013 | Foldvari et al. | |

FOREIGN PATENT DOCUMENTS

| | | |
|---|---|---|
| EP | 0 211 647 | 2/1987 |
| JP | 2006-525280 | 11/2006 |
| WO | WO-95/03787 | 2/1995 |
| WO | WO-99/11247 | 3/1999 |
| WO | WO-2004/096263 | 11/2004 |
| WO | WO-2004/103396 | 12/2004 |
| WO | WO-2005/087201 | 9/2005 |
| WO | WO-2012-065082 | * 5/2012 |

OTHER PUBLICATIONS

U.S. Appl. No. 13/965,158, filed Aug. 12, 2013, Kumar, Praveen.
U.S. Appl. No. 14/059,369, filed Oct. 21, 2013, Kumar, Praveen.
U.S. Appl. No. 14/059,373, filed Oct. 21, 2013, Kumar, Praveen.
ALTS group 2003. Östör AG, Natural history of cervical intraepithelial neoplasia: a critical review. Int. J. Gynecol. Pathol. 1993, 12:186-92.
Jones et al, "Quality management in gynaecologic cytology using interlaboratory comparison," Arch. Pathol. Lab. Med., (2000), 124(5):672-681.
Mantripragada, "A lipid based depot (DepoFoam technology) for sustained release drug delivery", Prog Lipid Res., 2002, 41(5):392-406.
Qui at al., "Multivesicular liposome formulations for the sustained delivery of interferon alpha-2B", Acta Pharmacol Sin., 2005, 26(11):1395-1401.
Stellato, "Intralesional recombinant alpha 28 interferon in the treatment of human papillomavirus-associated cervical intraepithelial neoplasia", Sexually Transmitted Diseases, 1992, 19(3):124-126.
Wang, "Instability, stabilization, and formulation of liquid protein pharmaceuticals", Int J Pharm., 1999, 185(2):129-188.
Yliskoski et al., "Topical treatment with human leukocyte interferon of HPV 16 infections associated with cervical and vaginal intraepithelial neoplasias", Bynecologic Oncology, 1990, 36(3):353-357.
Thitinan. S. et al., 'Interferon alpha delivery systems for the treatment of hepatitis C', International Journal of Pharmaceutics, vol. 369, pp. 121-135 (2009).
International Search Report and Written Opinion for Application No. PCT/US2014/050590 dated Dec. 8, 2014.

* cited by examiner

*Primary Examiner* — Frederick Krass
*Assistant Examiner* — Celeste A Roney
(74) *Attorney, Agent, or Firm* — Foley & Lardner LLP

(57) ABSTRACT

This invention relates to biphasic lipid-vesicle compositions and methods for treating cervical displasia by intravaginal delivery.

6 Claims, 3 Drawing Sheets

BIPHASIC LIPID-VESICLE COMPOSITIONS AND METHODS FOR TREATING CERVICAL DYSPLASIA BY INTRAVAGINAL DELIVERY

FIELD OF THE INVENTION

This invention relates to biphasic lipid-vesicle compositions and methods for treating cervical displasia by intravaginal delivery.

BACKGROUND OF THE INVENTION

Of the estimated 55 million Pap smears performed each year in the United States, more than 5% are reported as abnormal (ALTS study 2003). An estimated 800,000 women each year present with low-grade squamous intraepithelial lesions (LSIL) (Jones, B A, Davey D D. Quality management in gynaecologic cytology using interlaboratory comparison. Arch. Pathol. Lab. Med. 2000; 124(5):672-81).

These lesions will either progress with time to cervical intraepithelial neoplasia (CIN) 2-3 or invasive cancer, especially in women that present with the high-risk HPV-subtype, or regress with time in the absence of treatment. Of women diagnosed with LSIL, 25% will progress to CIN grade 2 or 3, 22-32% will have persistent CIN 1 and approximately 50%-70% will experience spontaneous regression of LSIL within 2 years (ALTS group 2003; Östör A G, Natural history of cervical intraepithelial neoplasia: a critical review. Int. J. Gynecol. Pathol. 1993, 12:186-92). Approximately 75% will experience spontaneous regression within 5 years.

Previously, U.S. Ser. No. 12/532,752 disclosed biphasic compositions for treating women with human papilloma virus (HPV) presenting with LSIL. These compositions represented a first-in-class treatment protocol and show significant promise. These biphasic compositions employ interferon alpha-2b in an oil-in-water emulsion found in both intra-vesicular and extra-vesicular phases. The interferon in both phases is oxidatively stabilized by the addition of methionine which unexpectedly partitions preferentially into the aqueous portion of the emulsion.

While these compositions are in clinical trials, accelerated shelf-life studies show that a longer shelf-life would be beneficial. Accordingly, it would be desirable to provide for improved compositions having an extended shelf-life.

SUMMARY OF THE INVENTION

This invention is directed, in part, to the discovery that pharmaceutically acceptable salts of arginine, which are not antioxidants per se, significantly improve the shelf-life of biphasic lipid vesicle compositions. Without being limited to any theory, it is contemplated that whereas a water soluble antioxidant, e.g., methionine, enhances stabilization of the interferon via its antioxidant effect, arginine stabilizes interferon alpha-2b by reducing the rate of formation of aggregates. Surprisingly, both arginine and a water soluble antioxidant such as methionine have been found to synergistically interact with the interferon to provide an enhanced shelf-life.

Accordingly, in one aspect, the invention includes a biphasic lipid vesicle composition for treating cervical dysplasia by intravaginal delivery. The composition includes a suspension of lipid-bilayer vesicles having entrapped therein, an oil-in-water emulsion, human interferon alpha-2b, and methionine. The extra-vesicular portion of the composition is also a water-in-oil emulsion containing human interferon alpha-2b and methionine. The interferon-alpha-2b in the composition preferably has a activity of between about 1-10 MIU (million international units) per gram composition and between 0.01 to 5 weight percent methionine. The intra-vesicular and extra-vesicular emulsion composition further comprises a sufficient amount of a pharmaceutically acceptable salt of arginine so as to enhance the shelf-life of the composition.

The composition, which may be in a cream form, contains in preferred embodiments, interferon alpha-2b at a specific activity between 1 and 10 MIU human interferon alpha-2b per gram composition, between 0.01 to 5 weight percent methionine, between 0.01 to 0.5 weight percent of a pharmaceutically acceptable salt of arginine. In each case, the weight percent of all components is a based on the total weight of the composition.

In further embodiments of the invention, the biphasic vesicle composition further comprises a water phase antioxidant which preferably is methionine. In various preferred aspects, the methionine is selected from L-methionine, D-methionine and racemic mixtures thereof. In exemplary embodiments, methionine is present in a concentration of from about 0.01 to 5 weight percent.

In further embodiments, the composition includes a suspension of lipid-bilayer vesicles having entrapped therein, an oil-in-water emulsion, human interferon alpha-2b, and a lipid antioxidant, a water phase antioxidant and arginine which is contemplated—partition in the water phase to act against aggregation of oxidatively stabilized interferon alpha-2b. During manufacturing of interferon alpha-2b, cream interferon alpha-2b may partition into various phases of formulation such as micelles, oil droplets, extra vesicular and intra-vesicular spaces and lipid bilayers. Similar to interferon alpha-2b, arginine may also partition in itself in these phases and thereby protect interferon alpha-2b from aggregation. The extra-vesicular portion of the composition is also a water-in-oil emulsion containing human interferon alpha-2b and antioxidant. The interferon-alpha-2b in the composition preferably has a specific activity of between about 1-10 MIU per gram composition and between 0.01 to 5 weight percent antioxidant, such as methionine. In further embodiments of the biphasic lipid vesicle, at least 30% of the interferon alpha-2b and the antioxidant is entrapped within the vesicles as part of the oil-in-water emulsion.

As noted above, the intra-vesicular and extra-vesicular emulsion composition preferably further comprises a sufficient amount of a pharmaceutically acceptable salt of arginine so as to enhance the shelf-life of the composition. In particular aspects, the pharmaceutically acceptable salt of arginine is L-arginine hydrochloride.

In another aspect, the invention includes a method of treating cervical dysplasia in the subject by administering the above composition intravaginally to the subject, at a dose of between 1-20 MIU interferon alpha-2b, and repeating the dosing at least 3 days/week, for a period of at least 4 weeks.

These and other features of the invention will be more fully appreciated when the following detailed description of the invention is read in conjunction with the accompanying drawings.

DETAILED DESCRIPTION OF THE INVENTION

Figure 1:
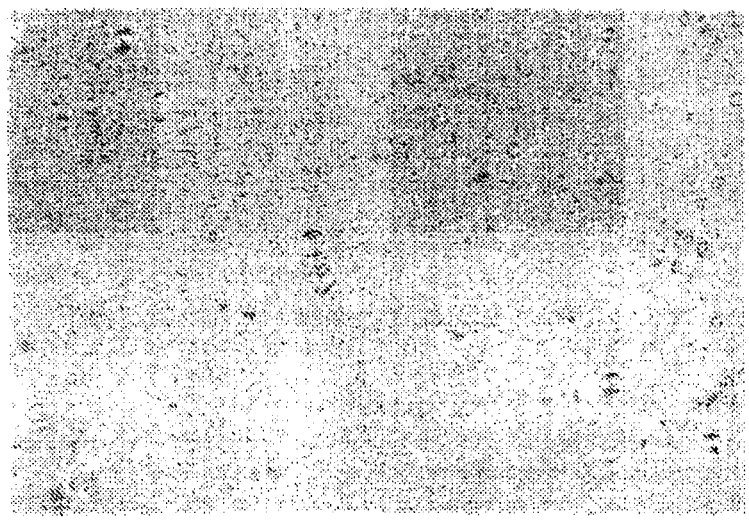
FIG. 1 is a scanned image, magnified 440X, of vesicles made for use as a topical lotion.

I. Biphasic Liposome Composition and Method of its Preparation

The invention relates to a lipid-bilayer or liposome or lipid vesicle composition for use in delivering an interferon, e.g., interferon alpha-2b by transmucosal delivery, e.g., by intravaginal administration, particularly in the treatment of cervical dysplasia.

A preferred method of preparing a multilamellar lipid vesicle of the invention is as follows. An oil and a consistency enhancer, stabilizers, surfactants and/or co-surfactants are admixed. In various embodiments, water and a surfactant are separately admixed. A water-soluble antimicrobial agent, for example methylparaben or propylparaben, a buffering agent, such as phosphates, and a chelating agent, such as EDTA, can also be dissolved in the water. These are heated gently, say to about 70° C., and then admixed and homogenized with the oil and consistency enhancer, stabilizers, surfactants and/or co-surfactants. This results in formation of an emulsion, with water as the continuous phase and the oil and consistency enhancer as the dispersed phase. It is desirable that the oil droplets shall be less than about 1 µm, especially less than about 0.5 µm, in diameter and if necessary the emulsion can be subjected to additional shear or to sonification to reduce the size of the droplets.

Separately there is prepared an anhydrous proliposome gel by admixing phospholipid, glycolipid and/or ceramide and a pharmaceutically acceptable hydrophilic solvent, e.g., propylene glycol, and heating them to form a melt. In the melt there may also be incorporated a material to enhance the strength of the lipid bilayers, for example cholesterol, a material to enhance penetration, for example monolauroyllysine, and a material to impart a charge to the lipid bilayers, for example stearic acid. A small amount of a lipid antioxidant can be incorporated in the melt. Lipid antioxidants are described in U.S. patent application Ser. No. 13/965,158 and entitled BIPHASIC LIPID-VESICLE COMPOSITIONS AND METHODS FOR TREATING CERVICAL DYSPLASIA BY INTRAVAGINAL DELIVERY which application is incorporated herein by reference in its entirety. The aqueous emulsion is added to the melt and the various components are subjected to agitation which results in formation of the desired multilamellar lipid vesicles having in the central core compartment an aqueous emulsion containing the oil and consistency enhancer as the dispersed phase.

A water-soluble biologically active material, and in particular, human interferon alpha-2b can be incorporated in solution in the aqueous phase of the emulsion, as discussed below. The interferon alpha-2b is incorporated into the aqueous phase to form a final composition having a specific activity of between 1-10 MIU per gram composition. The composition is also formulated to contain between 0.01 to 5 weight percent of an antioxidant such as methionine, e.g. 0.01-0.5 weight percent methionine, and this component may also be incorporated into the aqueous phase at a concentration effective to give the desired concentration in the final composition, and a chelating agent such as EDTA and/or an antioxidant and/or a protein stabilizer such as glycine. In exemplary embodiments, the composition is formulated to further comprise a sufficient amount of arginine and/or a pharmaceutically acceptable salt of arginine.

Formation of an Anhydrous Plastic Proliposome Gel

A liposome-forming component and other necessary excipients are melted with a pharmaceutically acceptable hydrophilic solvent, such as propylene glycol.

The expression "liposome-forming component" designates the substance or substances used as major component of the lipid bilayers. Typical liposome-forming components include glycolipids, lecithins, phospholipids, ceramides or mixtures thereof which are used as a primary ingredient in the formation of the lipid bilayer. However, other natural and synthetic compounds having the required amphipatic character can be incorporated with the phospholipid, glycolipid or ceramide, replacing some of these expensive materials, provided that the essential character of the lipid bilayers is not adversely affected. The choice of the appropriate materials is within the knowledge of the person skilled in the art. Examples include phosphatidylethanolamine, lysolecithin, lysophosphatidylethanolamine, phosphatidylserine, phosphatidylinositol, sphingomyelin, cardiolipin, phosphatidic acid and the cerebrosides, ether lipids and phytanols.

The liposomal formulations of the present invention preferably contain saturated and/or unsaturated phospholipids, more preferably phosphatidylcholine, lysophosphatidylcholine, phosphatidylserine, phosphatidylethanolamine, glycolipids and ceramides. The phospholipids are preferably in combination with a penetration enhancing agent such as monolauroyllysine, dipalmitoyllysine or methyl salicylate to achieve predominantly transdermal delivery potential.

A "fatty substance" can be used to enhance the strength of the lipid bilayers. Examples of useful fatty substances include steroids such as cholesterol, coprostanol, cholestanol and cholestane and long chain fatty acids ($C_{16}$ to $C_{22}$), especially saturated ones such as stearic acid. In addition to enhancing strength of the lipid bilayer, acids impart a negative charge. Saturated or unsaturated acids can be used. Other fatty substances that can be used include $C_{16}$ to $C_{22}$ fatty amines, fatty acylated proteins, fatty acylated peptides, fatty acylated PEG and derivatives. These fatty substances are incorporated with the abovementioned liposome-forming components and improve physical stability and appearance of the product.

The hydrophilic solvent is used as a plasticizer of the liposome-forming component and an aid to prepare a uniform melt. Examples of hydrophilic solvents include but are not restricted to propylene glycol, glycerol, polyethylene glycol having a molecular weight ranging between 300 and 8000, ethanol, and mixtures thereof. The resulting melt can be described as being an anhydrous plastic proliposome gel. This anhydrous plastic proliposome gel contains all the lipid phase ingredients and can be prepared and stored in advance in large quantities. It is a semisolid material with a homogenous consistency.

B. Formation of the Multilamellar Lipid Vesicles

Hydrophilic ingredients such as penetration enhancers, preservatives and the like, are prepared separately as an aqueous solution, which forms the continuous phase of an emulsion. This is added to the lipid phase melt, previously heated to the appropriate melting temperature that can range from 40° C. to 80° C., and vigorously mixed by any given technique which allows the achievement of the desired product size. Examples of mixing techniques include vortexing or propeller mixing. At this stage, it is also possible to incorporate (dissolve) solid biologically active agents that will be entrapped within the lipid bilayers.

This procedure is suitable for the preparation of various amounts of topical liposomal product. If vortex mixing is used as the agitation, up to about 20 g of the product can be prepared. If a laboratory scale propeller mixer is used, up to about 2 kg to 10 kg of the product can be made. This formulation procedure can also be adapted for large scale manufacturing. Hence, the propeller mixing technique can be directly scaled up by geometrically increasing the size of the vessel and the diameter of the propeller mixer. However, as the vessel size increases, the preferred set up would be a combination mixer, i.e. a high intensity mixer with propeller mixer and a scraped surface agitator. The aqueous phase can either be pumped from tank A to tank B containing the anhydrous plastic proliposome gel or the aqueous phase can be mixed with the emulsion prior to adding to Tank B at the required temperature and mixed. This procedure is suitable for the production of any topical liposomal product on a large scale.

Liposomal compositions can be prepared with the multilamellar lipid vesicles of the present invention by using appropriate pharmaceutical additives. For example, it might be required to add viscosity increasing agents to the final liposome preparation. The addition of other pharmaceutically acceptable compounds is within the purview of the person skilled in the art.

C. Characteristics of the Final Multilamellar Lipid Vesicle Product

A schematic representation of a multilamellar lipid vesicle prepared in accordance with the process described above is shown at FIG. 3. The multilamellar lipid vesicle, generally designated by reference numeral 2, is made of a series of spaced apart lipid bilayers 4, 6 and 8 which define a series of peripheral aqueous solution compartments 3 and 5. The smallest lipid bilayer 7 defines in its center a central core compartment 9. Although only six lipid bilayers are shown, it should be appreciated that the figure is simplified and schematic and in fact many more than six lipid bilayers are present.

Figure 3:
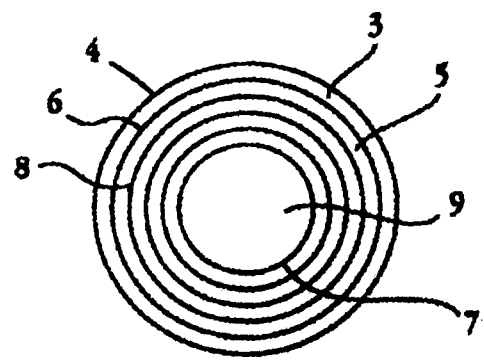
FIG. 3 is a schematic sectional view of a biphasic multilamellar lipid vesicle (MLV) with a central aqueous emulsion core.
Figure 4:
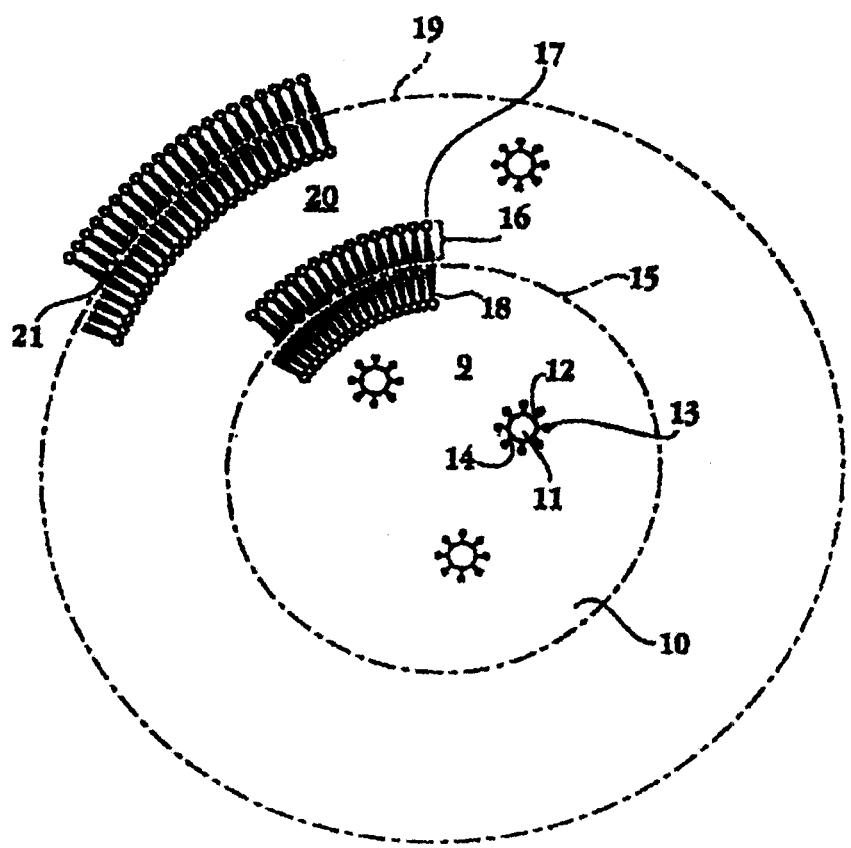
FIG. 4 is an enlarged portion of the MLV of FIG. 3.

FIG. 4 is an enlargement of the vesicle of FIG. 3 showing in more detail the central core compartment and parts of some of the lipid bilayers. The central core compartment 9 is occupied by an aqueous emulsion composed of water 10 as continuous phase and lipophilic droplets or fine solid particles 11 as dispersed phase. The lipophilic droplets or fine solid particles are surrounded by a layer of surfactant molecules 12, the hydrophilic portions 13 of each surfactant molecule extending into the aqueous phase and the hydrophobic portions being at the surface of the oil droplets.

Surrounding the core compartment is the innermost lipid bilayer 15. The lipid bilayer is composed of two layers of lipid molecules 16. Each lipid molecule 16 in a layer is oriented substantially parallel to adjacent lipid bilayers, and two layers that form a bilayer have the polar ends 17 of their molecules exposed to the aqueous phase and the non-polar ends 18 adjacent to each other. Between the innermost lipid bilayer 15 and the next innermost lipid bilayer 19 is a peripheral compartment 20 that is filled either with water or with the aqueous emulsion. As shown, surfactant surrounded lipophilic droplets or particles 11 can be present in the peripheral compartment 20.

Surrounding the peripheral compartment 20 is the next innermost lipid bilayer 19, which is in turn surrounded by a further peripheral compartment and a further lipid bilayer.

It will be appreciated that the biologically active ingredient, interferon alpha-2b, stabilizers, an anti-aggregant such as arginine and a water soluble antioxidant (e.g., methionine) will be present in the water of the aqueous emulsion in the central core compartment 9 and in the peripheral compartments 20. Other inactive ingredients that are lipophilic, such as consistency enhancers or uptake enhancers, can be present in the dispersed phase of the emulsion in the central compartment 9 and in the peripheral compartments 20. They can also be present in the interior of the lipid bilayers as shown at 21. The biologically active ingredient can constitute the lipophilic droplets 21, or the biologically active ingredient can be dissolved in a lipophilic solvent that forms droplets 21. Thus, the invention permits the topical application of biologically active ingredients that are water-soluble or water-insoluble.

In various aspects of the invention, an anti-aggregant, such as arginine, may be present in the intra-vesicular and extra-vesicular spaces of the multilamellar vesicles.

The term "stability" refers to the physical, chemical, and/or conformational stability of formulations of interferon of the invention (including maintenance of biological potency). Instability of a protein formulation may be caused by chemical degradation or aggregation of the protein molecules to form higher order polymers, deglycosylation, modification of glycosylation, oxidation or any other structural modification that reduces at least one biological activity of the compositions of the invention.

A "stable" or "stabilized" composition is one wherein the degree of degradation, modification, aggregation, loss of biological activity and the like, of proteins therein is acceptably controlled, and does not increase unacceptably with time. Preferably, the composition retains at least or about 60%, more preferably at least at or about 70%, most preferably at least at or about 80% of the labeled interferon activity over a period of 24 months. The stabilized interferon compositions of the invention preferably have a shelf-life of at least about 18 months, more preferably at least 20 months, still more preferably at least about 22 months and most preferably at least about 24 months when stored under refrigerated conditions (2° C.-8° C.).

In exemplary embodiments, a sufficient amount of an antioxidant, for example methionine, is employed to stabilize the interferon alpha-2b present in the intra-vesicular space in the central core compartment 9 as well as in the peripheral compartments 20 to provide oxidative stability to the interferon alpha 2b in the intra-vesicular space. Additionally, the antioxidant employed in this manner also serves to provides oxidative stability to the interferon alpha-2b retained in the extra-vesicular space. In various aspects, one or more antioxidants may be included in the formulations according to the invention, and in certain aspects a combination of two or more antioxidants is employed.

In particular embodiments, the antioxidant employed is L-methionine, although it is also contemplated that D-methionine can be used, or alternatively a racemic mixture of both. Thus, any stereoisomer (i.e., L, D or DL isomer) of methionine may be used in the compositions of the invention. Preferably, the L-stereoisomer is used. Analogues of methionine may also be used, the term "methionine analogue" referring to a derivative of the naturally occurring methionine, for instance, methionine derivatives with alpha and/or beta-amino substituted groups. In exemplary embodiments, the amount of methionine used in the composition preferably ranges from about 0.01 to about 5 weight percent based on the total weight of the composition. More preferably, the amount of methionine ranges from about 0.01 to about 0.5 weight percent based on the total weight of the composition.

The composition may further comprise at least one additional antioxidant to further stabilize interferon alpha-2b in the biphasic lipid vesicles. Additional antioxidants include, but are not limited to, ascorbic acid and its salts, ascorbyl palmitate, ascorbyl stearate, N-acetylcysteine, benzyl isothiocyanate, caffeic acid, sodium metabisulfate, benzyl alcohol and tocopherols, including alpha-tocopherol and its salts. Further examples of antioxidants that may be used include:

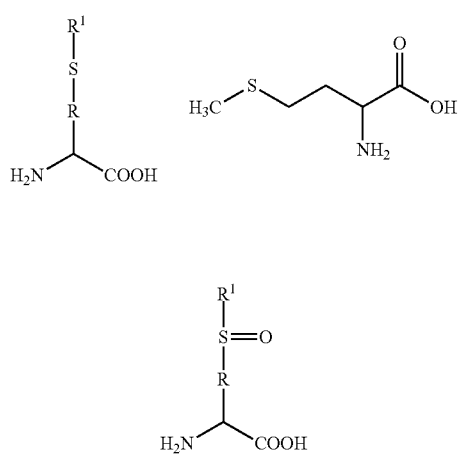

where R is $C_1$ to $C_6$ alkylene and $R^1$ is $C_1$ to $C_6$ alkyl. Additionally, substitution of alpha-amino acids with their beta-amino acid analogues and/or homologs can also be used as antioxidants.

Further, the term "anti-aggregant" as used herein refers to any biocompatible compound that inhibits and/or reduces the aggregation of interferons, e.g., formation of aggregates of interferon alpha-2b. The process of aggregation (e.g., interferon aggregation) can be influenced by a variety of factors, such as but not limited to physicochemical stresses, including heat, pressure, pH, agitation, shear forces, freeze-thawing, dehydration, heavy metals, oxygen, phenolic compounds, silicon oil, denaturants and the like.

The term "guanidine" as used herein includes guanidine and derivatives thereof (e.g., in which the hydrogen atom attached to the amidino nitrogen (=NH) is replaced by substituted or unsubstituted carboxyl groups, substituted or unsubstituted amino groups, substituted or unsubstituted alkyl groups, substituted or unsubstituted heteroalkyl groups, substituted or unsubstituted aryl groups, and substituted or unsubstituted heteroaryl groups). In preferred embodiments, the anti-aggregants include compounds that contain a guanidine group, for example, guanidinoacetic acid, substituted or unsubstituted guanidinobenzoic acid, guanidine carbaniedine, guanidine acetate, guanidine amine, guanidine carbonate, guanidine nitrate, guanidine hydrochloride, arginine, arginine analogues and the like. Arginine that has been derivatized at the carboxy or alpha-amino groups is also contemplated. In a preferred embodiment, L-arginine hydrochloride is used as an anti-aggregant.

It has now been found that the addition of a pharmaceutically acceptable salt of arginine imparts enhanced shelf-life to the composition by reducing the formation of aggregates. The arginine employed is preferably a pharmaceutically acceptable salt of L-arginine although it is contemplated that D-arginine can also be used, as can a racemic mixture of both. Suitable pharmaceutical salts include, by way of example only, well known organic and inorganic salts such as hydrochloride salts, hydrobromide salts, $C_1$ to $C_6$ carboxylic acid salts such as acetate, proprionate, succinate, oxalate, benzoate salts. A particularly preferred salt is the hydrochloride salt of L-arginine as this allows arginine to incorporate into the aqueous solution of interferon alpha-2b. The amount of pharmaceutically acceptable salt of arginine used in the composition preferably ranges from about 0.01 to about 5 weight percent based on the total weight of the composition. More preferably, the amount of the pharmaceutically acceptable salt of arginine ranges from about 0.1 to about 0.5 weight percent based on the total weight of the composition.

Without being limited to any theory, it is believed that the arginine allows interferon alpha-2b to remain in the monomer form and inhibits the formation of aggregates in the composition thereby extending the shelf-life of the composition.

In particular embodiments, compounds containing a guanidine group, such as arginine, are suitable anti-aggregating stabilizing agents for interferon alpha-2b. The term "salts" herein refers to both salts of carboxyl groups and to acid addition salts of amino groups of the stabilizing agents described above or analogs thereof. In some aspects, the arginine employed is a pharmaceutically acceptable salt of L-arginine, although it is contemplated that D-arginine can also be used, or alternatively a racemic mixture of both. In other embodiments, suitable pharmaceutical salts include, by way of example only, well known organic and inorganic salts such as hydrochloride salts, hydrobromide salts, $C_1$ to $C_6$ carboxylic acid salts such as acetate, proprionate, succinate, oxalate, or benzoate salts. A particularly preferred salt is the hydrochloride salt of L-arginine. The amount of pharmaceutically acceptable salt of arginine used in the composition preferably ranges from about 0.01 to about 5 weight percent based on the total weight of the composition. More preferably, the amount of the pharmaceutically acceptable salt of arginine ranges from about 0.01 to about 0.5 weight percent based on the total weight of the composition.

The composition, containing the pharmaceutically acceptable salt of arginine is preferably, formed under conditions in which at least about 30 weight percent, and preferably between about 40 and 70 weight percent of these aqueous components is present in liposome entrapped form, as opposed to being carried in the extra-vesicular bulk phase of the composition. These levels of entrapment can be achieved by various known strategies, e.g., forming the liposomes by a reverse-phase evaporation method and/or encapsulating the aqueous phase material at a high concentration of liposome-forming lipids, thus minimizing the amount of bulk aqueous phase.

FIG. 1 is a scanned image, magnified 440×, of vesicles made for use as a topical lotion. This product displayed the consistency of a lotion or semi-solid cream. Inspection of the scanned image reveals multilamellar structures with uniform size distribution. These have displayed physical stability for extended periods of time of more than one year.

Figure 2A:
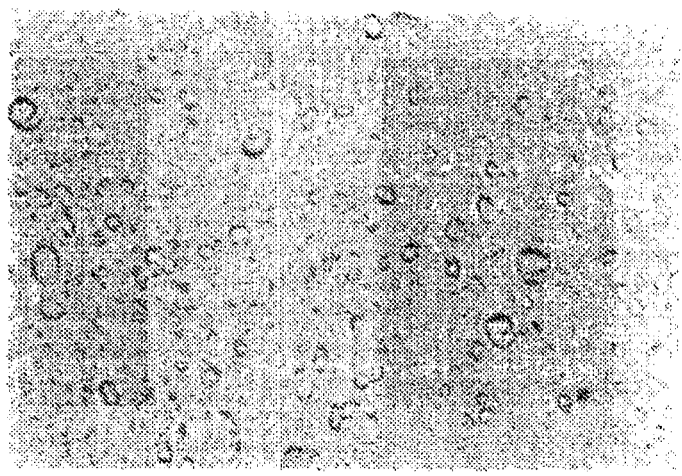
FIG. 2A is a scanned image of multilamellar liposomes prepared using an "anhydrous plastic proliposome-gel" ('melt' or 'fusion') method.
Figure 2B:
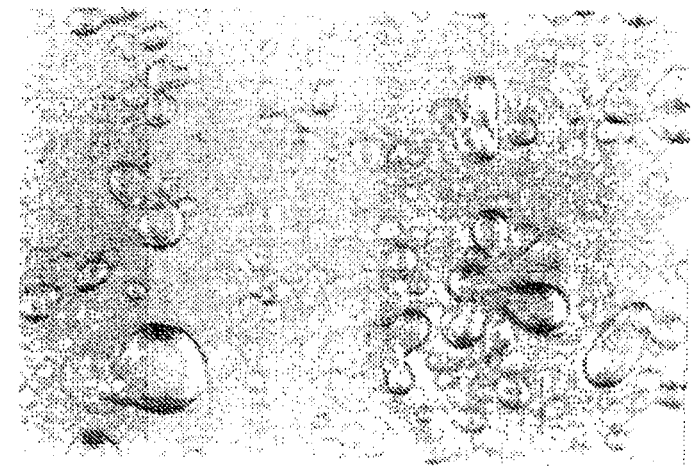
FIG. 2B is a scanned image of multilamellar liposomes, the same composition as in 2A, but prepared by a solvent evaporation method.

In order to demonstrate the difference in properties observed in the liposome population produced in accordance with a preferred method, comparative tests were conducted between two liposome compositions prepared from the same ingredients but using in one case the solvent evaporation method and in the other case the preferred anhydrous proliposome gel method. FIG. 2A is a scanned image of the liposome population prepared using the anhydrous proliposome gel ('melt' or 'fusion') method and FIG. 2B is a scanned image of the liposome population prepared using the solvent evaporation method. As can be seen, the liposome population obtained using the anhydrous plastic proliposome gel method has a liposome size distribution which is substantially more uniform than that obtained using the solvent evaporation method. Also, minimal amounts of aggregated or fused liposomes are formed when using the anhydrous plastic proliposome gel method, whereas large aggregates can be observed in the liposome population obtained using the solvent evaporation method.

In some embodiments of the invention, the lipophilic substance is an oil or solid/semisolid lipophilic consistency enhancer which can be encapsulated into liposomes. As solid or semisolid lipophilic consistency enhancers there are mentioned fatty alcohols, waxes, fatty alcohol fatty acid esters, glyceride esters, white petrolatum and mixtures thereof. Examples of oils which have successfully been encapsulated into liposomes include pentaerythritol tetracaprylate/caprate, pentaerythritol tetraisostearate, cetearyl octanoate and canola oil, jojoba oil, peanut oil, rice bran oil, cottonseed oil, sunflower oil, corn oil, walnut oil, avocado oil, peru balsam, clove oil and eugenol. Plant extracts based on oil have also been successfully incorporated into liposomes. Solid/semisolid lipophilic consistency enhancer ingredients can be selected from waxes, fatty alcohols, fatty acid esters, glyceryl stearate, petrolatum or combinations thereof. Specific examples of preferred consistency enhancers include beeswax, glyceryl tribehenate, glyceryl stearate, stearyl heptanoate, stearyl palmitate, cetyl alcohol, stearyl alcohol, myristyl myristate, behenyl erucate and cetyl palmitate.

The viscosity of a composition of vesicles in accordance with the invention and containing a consistency enhancer is greater than the viscosity of corresponding vesicles that do not include a consistency enhancer but are otherwise identical. By varying the amount of consistency enhancer it is possible to achieve virtually any required viscosity, from a relatively mobile liquid, to a "lotion", to "creamy" to "thick cream". The amounts of consistency enhancer required to achieve a particular viscosity of the composition can be determined by routine experiment.

The surfactant used to coat the oil droplet or the solid/semisolid lipophilic consistency enhancer ingredients is important for the successful encapsulation of a lipophilic core into multilamellar lipid vesicles. About 30 different types of surfactants were screened and primary cationic emulsifiers were found to give the most acceptable results. The most preferred surfactant is benzalkonium chloride or other cationic surfactants such as benzethonium chloride, cetylpyridinium chloride, cetrimide. Nonionic or amphoteric surfactants can also be used, such as naturally derived emulsifiers: PEG-60 almond glycerides, avocado oil diethanolamine, ethoxylated jojoba oil (PEG-40 Jojoba acid and PEG-40 Jojoba alcohol); polyoxyethylene derivatives: polyoxyethylene (20) sorbitan monooleate, polyoxyethylene (20) sorbitan monostearate; lanolin derivatives: polychol 20 (Laneth 20), polychol 40 (laneth 40); neutral phosphate esters: PPG-cetyl ether phosphate, DEA oleth-3 phosphate. It is also possible to use anionic surfactants such as acylglutamates: TEA-cocoyl glutamate, sodium lauroyl glutamate, sodium hydrogenated tallow glutamate and sodium cocoyl glutamate. It is desirable that the surfactant has a high critical micellar concentration (CMC).

When preparing the lipophilic substance-in-water emulsion, the hydrophilic ingredients and surfactants are all incorporated in water. Once the water phase of the emulsion has been prepared, the oil and/or solid/semisolid lipophilic ingredients are added to the water in a homogenizer for a period of time ranging from 5 to 30 minutes to obtain relatively small droplet size. Preferred droplet size ranges from 0.1 µm to 1 µm, most preferably below about 0.5 µm. The lipid phase melt (anhydrous plastic proliposome gel) is then heated and the lipophilic substance-in-water emulsion is added and vigorously mixed by either vortexing or propeller mixing depending on the product size.

The formulation procedure described above can be easily adopted for large scale manufacturing. The propeller mixing approach can be directly scaled up by geometrically increasing the size of the vessel and the diameter of the propeller mixer. However, as the vessel size increases, a preferred set up might be a combination mixer such as a high intensity mixer with propeller mixer and a scraped surface agitator. In a large scale operation, the lipophilic substance (called the oil phase)-in-water emulsion can be pumped from a first tank into a second tank containing the anhydrous plastic proliposome gel at the required temperature and mixed.

With the multilamellar lipid vesicle of the present invention, oil droplets containing solubilized lipophilic biologically active compounds or oily plant extracts can be delivered through liposome encapsulation. Furthermore, the possibility of multicompartment encapsulation provides drug release over extended periods of time. Also, encapsulation of lipophilic solid/semisolid consistency enhancers into the central lipophilic core compartment provides enhanced viscosity to the final liposome composition. In this case, the addition of viscosity-increasing agents in the final liposome preparation can be avoided.

Overall, the preparation of multilamellar lipid vesicles with a central emulsion core component provides a physically stable, uniform liposome composition. The composition has a viscosity that is suitable for topical administration and can be easily manufactured on a large scale.

Without being limited to any theory, it is believed that the biphasic nature of this composition provides for both topical treatment of the mucosal layer as well as penetration of the vesicles into the mucosal layer and endocytosis to gain access to the intracellular space. This is critically important as the HPV resides throughout the mucosal layer. This binary treatment of the mucosal layer is achieved by the biphasic nature of the composition which allows the extra-vesicular emulsion to target the topical mucosal layer while the vesicles can penetrate into the lipophilic mucosa and promote endocytosis which will result in vesicle rupture.

In addition, the biphasic nature of the composition and the oil-in-water emulsion used permits the clinician to provide for a cream or lotion with a viscosity such will be retained at the point of application for a sufficient period of time to allow therapeutic release of the interferon alpha 2b.

D. Exemplary IFN-Alpha-2b Cream Formulations for Intravaginal Use

Table 1 gives the components for a comparative composition lacking an anti-aggregating stabilizing agent such as arginine in a lipid-bilayer composition where the amount of each component is expressed in units of mg/g final composition, and given in both ranges and exemplary quantities (parentheses). The resulting composition is referred to in the studies below as “Formulation Q25C”, and is formed as detailed below.

TABLE 1

| Component | Quantity mg/g | |
|---|---|---|
| Active | | |
| Interferon alpha-2b Drug Substance | 0.01-5 | (0.808) |
| Excipients and protective agents | | |
| Benzalkonium Chloride 50% Solution | 1-10 | (2) |
| Butylated Hydroxytoluene | 0.1-0.5 | (0.102) |
| Cetyl Alcohol | 2-40 | (20.514) |
| Cholesterol | 2-40 | (20) |
| Edetate Disodium Dihydrate | 0.1-0.5 | (0.103) |
| Glycerol Monostearate 40-55, Type 1 | 5-50 | (30.771) |
| Glycine | 0.1-5 | (1) |
| L-Methionine | 0.1-5 | (1.126) |
| Methylparaben | 0.1-5 | (1.538) |
| Olive Oil, Super Refined | 10-70 | (51.285) |
| PEG-40 Castor Oil, Hydrogenated | 10-70 | (51.285) |
| Sodium phosphate, Dibasic, Heptahydrate | 1-2 | (1.670) |
| Sodium phosphate, Monobasic, anhydrous | 0.25-1 | (0.480) |
| Phospholipon 90H | 60-200 | (100) |
| Propylene Glycol | 30-100 | (69.95) |
| Propylparaben | 0.1-1 | (0.513) |
| Purified Water | Q.S. to 1000 | (646.846) |

Table 2 gives the components in one exemplary lipid-bilayer composition formed in accordance with the invention, where the amount of each component is expressed in units of mg/g as both ranges and exemplary quantities. The resulting composition is referred to as "Formulation Q25C-RH."

TABLE 2

| Excipients | Range (mg/g) | Exemplary quantity (mg/g) |
|---|---|---|
| PEG-40 Castor Oil, Hydrogenated, USP/NF | 10-70 | 51.285 |
| Benzalkonium chloride 50% solution, NF | 1-10 | 2.00 |
| Methylparaben, NF | 0.1-5 | 1.538 |
| Propylparaben, NF | 0.1-1 | 0.513 |
| L-methionine, USP | 0.1-5 | 1.126 |
| Edetate Sodium, dihydrate, USP | 0.1-0.5 | 0.103 |
| Phosphate buffer (composed of Sodium phosphate dibasic heptahydrate USP and Sodium phosphate Monobasic USP, anhydrous) | 1-70 | 51.285 |
| Purified water, USP | Q.S. to 1000 | 596.72 |
| Olive oil, Super refined, NF | 10-70 | 51.285 |
| Glycerol monostearate 40-55, Type I, EP | 5-50 | 30.771 |
| Cetyl alcohol, NF | 2-40 | 20.514 |
| Lipid Antioxidant, NF | 0.1-0.5 | 0.102 |
| Phospholipon 90H | 60-200 | 100.00 |
| Cholesterol, NF | 2-40 | 20.00 |
| Propylene glycol, USP | 30-100 | 69.95 |
| Glycine, USP | 0.1-5 | 1.0 |
| L-arginine hydrochloride, USP | 0.1-5 | 1.0 |
| Nitrogen, NF | 0 to Q.S. | n/a |
| Interferon alpha 2b | 0.01-5 | 2 MIU/g |

Description of the Manufacturing Process for Q25C-RH.

Step 1. Preparation of oil-in-water submicron emulsion (System A): Olive oil, glycerol monostearate 40-55 Type I, cetyl alcohol and butylated hydroxy toluene are melted together at 75° C.±5° C. The aqueous component of the emulsion including purified water, PEG-40 castor oil hydrogenated, benzalkonium chloride 50% solution, methylparaben, propylparaben, L-methionine, edetate disodium dihydrate, and phosphates are heated together in a stainless steel vessel at 75° C.±5° C. while stirring until the ingredients are dissolved. The oil component (75° C.±5° C.) is then added to the aqueous component (75° C.±5° C.) gradually, while mixing to form a coarse emulsion. Coarse emulsion is then homogenized by processing through a Microfluidizer until a homogeneous emulsion is formed. This submicron emulsion is cooled down to 8° C.-12° C.

Step 2: Preparation of the Lipid Phase: The Lipid Phase is prepared by melting Phospholipon 90H, cholesterol and butylated hydroxy toluene with propylene glycol in a mixer by heating to about 80-90° C. while mixing at a slow speed. The mixing and heating of the Lipid Phase ingredients is continued until a clear melt is formed which is then cooled to about 60° C.

Step 3: Preparation of the Aqueous Phase: The required quantity of IFN alpha-2b stock solution is added and mixed gently with a mixture of L-methionine, glycine, L-arginine hydrochloride and purified water.

Step 4: Product Formulation: The Aqueous Phase containing interferon alpha-2b (from Step 3) is added to the System A (from Step 1) in a stainless steel jacketed mixing tank. This mixture is maintained between 8° C.-12° C. while the mixture is mixed slowly and purged with nitrogen gas. The cooled mixture of System A-Aqueous Phase is rapidly added to the Lipid Phase which is being mixed at high speed in the mixer. Mixing proceeds for 10-15 minutes while the temperature of the mixture is maintained about 57-60° C. The bulk product thus formed is slowly mixed and cooled to 19° C.-25° C. in a mixer. The product is transferred from the mixer into a stainless steel storage vessel and purged with nitrogen gas. The bulk product is filled into 5 g polypropylene tubes or polypropylene pre-fill applicators. The tubes or applicators are purged with nitrogen and then the required amount of the product is filled into the tubes or pre-fill applicators, which are thermally sealed in case of tubes whereas prefilled applicators are capped. The filled tubes or pre-filled applicators of Interferon alpha-2b Cream drug product are stored at 5° C.±3° C.

A comparison of the shelf-life (5° C.±3° C.) of three formulations is provided in the following Table 3. During the shelf-life of the product Interferon alpha-2b content as measured by RP-HPLC must remains within 80% to 100% of label claim. In Q25C-RH (with l-arginine HCl) the interferon alpha-2b remains within specifications until 24 months under real storage conditions whereas Q25C (without l-arginine HCl) has a shelf life of only 15 months. Thus, the addition of L-arginine HCl to the formulation significantly improves the product shelf life. Both accelerated studies (Table 4) and real time storage stability studies (Table 3) show that l-arginine improves the stability of Interferon alpha-2b in the product.

TABLE 3

| Formulation | Time Period (months) | Shelf life | % of Initial IFNa2b Interferon alpha-2b Content (5° C. ±3° C.) |
|---|---|---|---|
| Q25C (without Arginine) Lot #8P5292 | 0 | Acceptable | 100 |
| | 1 | Acceptable | 104.59 |
| | 2 | Acceptable | 101.83 |
| | 3 | Acceptable | 100.92 |
| | 6 | Acceptable | 97.25 |
| | 9 | Acceptable | 88.07 |
| | 12 | Acceptable | 83.49 |
| | 15 | Acceptable | 81.65 |
| | 18 | Not acceptable | 76.15 |

TABLE 3-continued

| Formulation | Time Period (months) | Shelf life | % of Initial IFNa2b Interferon alpha-2b Content (5° C. ±3° C.) |
|---|---|---|---|
| | 24 | Data not available | Data not available |
| Q25C-RH (with Arginine) Lot #9A5541 | 0 | Acceptable | 100 |
| | 1 | Acceptable | 97.52 |
| | 2 | Acceptable | 95.87 |
| | 3 | Acceptable | 92.56 |
| | 6 | Acceptable | 89.25 |
| | 9 | Acceptable | 91.74 |
| | 12 | Acceptable | 87.60 |
| | 15 | Acceptable | 85.95 |
| | 18 | Acceptable | 84.30 |
| | 25 | Not Acceptable | 78.51 |
| Q25C-RH (with Arginine HCl) Lot #904C03A | 0 | Acceptable | 100 |
| | 1 | Acceptable | 94.02 |
| | 2 | Acceptable | 91.45 |
| | 3 | Acceptable | 90.60 |
| | 6 | Acceptable | 90.60 |
| | 9 | Acceptable | 86.32 |
| | 12 | Acceptable | 89.74 |
| | 15 | Acceptable | 87.18 |
| | 18 | Acceptable | 86.32 |
| | 24 | Acceptable | 81.20 |

TABLE 4

| Formulation (months) | Time Period | % of Initial IFNa2b Interferon alpha-2b Content (40° C. ±5° C./70%RH ±5%) |
|---|---|---|
| Q25C (without Arginine) F2-012110-Q25C (control) | 0 | 100 |
| | 1 | 40.39 |
| | 2 | 16.09 |
| | 3 | 9.62 |
| Q25C-RH (with Arginine) F2-012010-Q25C-l (with l-arginine) | 0 | 100 |
| | 1 | 63.00 |
| | 2 | 32.52 |
| | 3 | 19.64 |
| Q25C-RH (with Arginine HCl) F2-012010-Q25C-2 (with l-arginine HCl) | 0 | 100 |
| | 1 | 59.59 |
| | 2 | 36.93 |
| | 3 | 23.43 |

Table 4. Accelerated stability (40° C.±5° C./70% RH±5%) data of interferon alpha-2b content (%) as measured by RP-HPLC in formulations Q25C, Q25C-RH (with l-arginine) and Q25C-RH (with L-arginine HCL). Table 4 demonstrates that addition of L-arginine has a significant effect on the stability of interferon alpha-2b in the formulation.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

Although the invention has been described with respect to particular embodiments, it will be apparent to those skilled in the art that various changes and modifications can be made without departing from the invention.

What is claimed is:

1. A biphasic vesicle composition comprising:

(a) a first phase comprising an oil-in-water emulsion which oil-in-water emulsion comprises oil in a water phase, wherein a sufficient amount of oil is employed to form a composition suitable for topical application, and wherein the water phase comprises interferon alpha-2b, an antioxidant and an anti-aggregant; and (b) a second phase comprising multilamellar lipid vesicles suspended in said first phase wherein said vesicles contain entrapped therein a composition comprising an oil-in-water emulsion wherein the oil-in-water emulsion comprises a water phase comprising interferon alpha-2b, an antioxidant and an anti-aggregant, wherein the composition comprises a therapeutically effective amount of said interferon alpha-2b, and wherein said anti-aggregant preserves interferon alpha-2b in the monomeric form and the anti-aggregant is arginine or a pharmaceutically acceptable salt thereof.

2. The biphasic vesicle composition of claim 1, wherein the antioxidant is selected from the group consisting of L-methionine, D-methionine and racemic mixtures thereof.

3. The biphasic vesicle composition of claim 1, wherein the anti-aggregant is a pharmaceutically acceptable salt of arginine.

4. The biphasic vesicle composition of claim 3, wherein the pharmaceutically acceptable salt of arginine is L-arginine hydrochloride.

5. The biphasic vesicle composition of claim 2, wherein the L-methionine is present in the composition in an amount of 0.1 to 5 mg/g.

6. The biphasic vesicle composition of claim 4, wherein the L-arginine hydrochloride is present in the composition in an amount of 0.1 to 5 mg/g.

* * * * *